(12) United States Patent
Afriat et al.

(10) Patent No.: US 6,811,569 B1
(45) Date of Patent: Nov. 2, 2004

(54) EXPANSIBLE ACETABULAR PROSTHESIS WITH DOUBLE MOBILITY

(75) Inventors: Jacques Afriat, Narbonne (FR); Jean-Louis Bensadoun, Lezigneux (FR)

(73) Assignee: Proconcept SA, Courthezon (FR)

( * ) Notice: Subject to any disclaimer, the term of this patent is extended or adjusted under 35 U.S.C. 154(b) by 0 days.

(21) Appl. No.: 10/129,813

(22) PCT Filed: Nov. 9, 2000

(86) PCT No.: PCT/FR00/03115

§ 371 (c)(1),
(2), (4) Date: Sep. 4, 2002

(87) PCT Pub. No.: WO01/35873

PCT Pub. Date: May 25, 2001

(30) Foreign Application Priority Data

Nov. 19, 1999  (FR) .............................. 99 14543

(51) Int. Cl.$^7$ .................................................. A61F 2/32
(52) U.S. Cl. ............................ 623/22.32; 623/22.38; 623/22.24; 623/22.28
(58) Field of Search ........................ 623/22.21, 22.24, 623/22.26, 22.28, 22.3, 22.32, 22.38

(56) References Cited

U.S. PATENT DOCUMENTS

| | | | | |
|---|---|---|---|---|
| 4,822,369 A | * | 4/1989 | Oueveau et al. | 623/22.14 |
| 4,834,759 A | * | 5/1989 | Spotorno et al. | 623/22.3 |
| 4,878,918 A | * | 11/1989 | Tari et al. | 623/22.35 |
| 4,969,910 A | * | 11/1990 | Frey et al. | 623/22.33 |
| 5,108,448 A | * | 4/1992 | Gautier | 623/22.26 |
| 5,658,345 A | * | 8/1997 | Willi | 623/22.26 |
| 5,879,401 A | * | 3/1999 | Besemer et al. | 623/22.28 |
| 6,146,425 A | * | 11/2000 | Hoermansdoerfer | 623/22.31 |
| 6,231,612 B1 | * | 5/2001 | Balay et al. | 623/22.31 |
| 6,368,354 B2 | * | 4/2002 | Burstein et al. | 623/22.28 |
| 6,475,243 B1 | * | 11/2002 | Sheldon et al. | 623/22.28 |
| 6,610,097 B2 | * | 8/2003 | Serbousek et al. | 623/22.24 |
| 2001/0037156 A1 | * | 11/2001 | Burstein et al. | 623/22.28 |
| 2003/0105529 A1 | * | 6/2003 | Synder et al. | 623/22.24 |

FOREIGN PATENT DOCUMENTS

| | | |
|---|---|---|
| EP | 0 486 403 | 5/1992 |
| EP | 0 640 325 | 3/1995 |
| EP | 0803234 A1 * | 10/1997 |
| FR | 2 645 433 | 10/1990 |
| FR | 2 680 674 | 3/1993 |
| FR | 2 700 946 | 8/1994 |
| WO | WO 97/38650 | 10/1997 |

* cited by examiner

Primary Examiner—Pedro Philogene
Assistant Examiner—David A Bonderer
(74) Attorney, Agent, or Firm—Young & Thompson

(57) ABSTRACT

An acetabular prosthesis (1) includes a hollow hemispherical artificial acetabular cup (2) having expansion slots distributed over its periphery, and provided with teeth ($11n$,= 1–3) on the outer surface, a threaded intermediate element (3) and a plastic insert (4). The intermediate element (3) is a hollow core with an outer hemispherical surface capable of being urged in contact against at least an internal meridian generatrix of each segment defined between the slots; the inside part close to the orifice of the acetabular cup (2) has a thread wherein is screwed the intermediate core (3); the internal diameter of the acetabular cup (2) orifice of the acetabular cup (2) in reception position before the intermediate element (3) is screwed, is smaller than the external diameter of the intermediate element (3).

15 Claims, 3 Drawing Sheets

EXPANSIBLE ACETABULAR PROSTHESIS WITH DOUBLE MOBILITY

BACKGROUND OF THE INVENTION

The subject of the present invention is an expansible acetabular prosthesis with double mobility.

The technical field of the invention is the production of surgical equipment implantable in the human body.

The main application of the invention is the production of a hip prosthesis for replacing the cotyloid cavity of the hip bone, the whole prosthesis being intended to be anchored without cement.

Total hip prostheses comprise two elements:

1. The femoral stem: this component replaces the head and neck of the femur. A stem, forming a continuation of the neck, ensures anchoring thereof in the femoral bone, with or without cement.

2. The acetabular component: this replaces the osseous acetabulum and articulates with the prosthetic femoral head. A hemispherical cavity forms the sliding surface. This element can be made in one piece from metal, polyethylene or ceramic. However, to allow it to be fixed without cement, many models are made up of the following two elements:

a) a metal cup fixed in the bone, b) a plastic insert, in particular of polyethylene, fixed in the cup and articulating with the prosthetic head.

The problems encountered in surgical practice are the wear between the femoral head and the acetabular component, and also the fixation of the metal cup in the bone and the wear observed between the insert and the metal cup.

A number of ways of fixing the metal cup are presently employed, in particular sealing (a), impaction by force (b), screwing (c), or fixation by expansion (d), all of which are discussed below.

a) Sealing involves interposing an acrylic-type cement between the bone and the cup, which anchors in the bone and ensures the fixation of the component. However, this technique has disadvantages associated with the characteristics of the cement and of the bone and can lead in the medium term or long term to loosening.

b) Impaction by force involves press-fitting the metal cup into a bone cavity prepared with the aid of hemispherical reamers which calibrate the osseous acetabular cup to a diameter which is slightly smaller than that of the metal cup.

A coating or roughening of the outer surface of this cup improves the immediate mechanical stability of the cup and permits secondary stabilization by regrowth of bone. However, this initial mechanical stability is uncertain because it largely depends on the way in which the bone is prepared and especially on its hardness.

Most of the models therefore propose a complementary fixation recommended in cases where the press-fit retention is deemed insufficient. This fixation is ensured by screws which are placed in the bone via holes formed in the metal cup.

This technique of impaction by force has the following disadvantages:

the possible micro-movements between the screw and the metal cup can release particularly damaging metal products of wear, and the possible contact between the screw head and the insert is a possible source of wear and creep. Another problem is the creep of the insert (if it is made of polyethylene) relative to the screw holes, since this produces debris from wear which can migrate through the screw holes and lead to progressive osteolysis, which promotes mobilization of the implant.

c) Screwing of the acetabular cup involves using a metal cup with a threading on its outer surface, which threading is screwed into the bone. This method of fixing is little used at present because the position of the component is uncertain at the time of fitting. This is because the press-fit or screw-in acetabular cups cannot be fitted with precision because their positioning can be deviated by the bone during fitting.

d) In fixation by expansion, a metal cup is used which is designed to be opened by an intermediate element of metal or polyethylene situated between the cup and the insert, for example a ring.

Different types of acetabular prostheses fixed by expansion are known, and these comprise three elements, which are:

an artificial acetabular cup which is a cup provided with expansion slots which are symmetrically and uniformly distributed at angles over its periphery and which define segments or portions of a spherical cap sector;

a threaded intermediate element which is:

a) a ring intended to be screwed into the acetabular cup, as is described in patent application EP 486 403, or b) an intermediate core which comprises a threaded finger forming an appendix on its pole and which cooperates with a tapped hole in the artificial acetabular cup, as is described in patent application FR 2 700 946;

a friction insert which bears or engages on said intermediate element having a sliding surface in the shape of a hemispherical cavity, and in which an artificial head ball engages to restore the articulation of the hip.

The present invention concerns expansible acetabular prostheses with three elements, as are described above. More particularly, the present invention concerns acetabular prostheses with three elements substantially of spherical cap shape.

With the expansible acetabular prostheses which are presently available, the plastic insert which has to take up all the loading on the hip may creep and thus deform inside the acetabular cup.

In the case of an intermediate element with a continuous surface which better supports the insert, the acetabular cup is fixed by screws and this again does not ensure good overall stability: the reason being that the components of the prosthesis retain a certain mobility and elasticity which are also incompatible with good stability over time.

SUMMARY OF THE INVENTION

The object of the present invention is to remedy these disadvantages in particular, and the present invention aims to make available a prosthesis having:

improved mechanical stability, easier and more precise fitting in the bone, reduced wear of the components, the possibility of permitting double mobility by virtue of an insert which is movable in the intermediate element.

To do this, the subject of the present invention is an acetabular prosthesis comprising:

a hollow artificial acetabular cup, preferably with an outer surface of the spherical cap type, in particular hemispherical, having expansion slots distributed over its periphery;

an intermediate cup-shaped element, with an inner surface in the shape of a spherical cap, in particular hemispherical;

a hollow insert with outer and inner surfaces of spherical cap shape, preferably hemispherical, fitting in the intermediate element;

said acetabular cup and said intermediate element comprise screwing means so that the outer surface of said intermediate element can come into congruent contact, by screwing, against at least one internal meridian generatrix of each segment delimited by two of said consecutive slots, said means of screwing said intermediate element into said acetabular cup comprise a peripheral threading formed on the inner surface of the acetabular cup near its opening, in which threading said intermediate element is screwed with the aid of a complementary threading on its outer surface near its opening, the internal diameter of the opening of said acetabular cup, in the standby position before screwing of said intermediate element, is smaller than the external diameter of said intermediate element, and said acetabular cup is equipped with bone-anchoring teeth on its outer face.

This configuration of the acetabular prosthesis according to the invention in which the intermediate element bears in contact on at least one internal meridian generatrix of the internal cavity of the artificial acetabular cup permits a good distribution of the forces and stresses across the entire surface of the artificial acetabular cup.

In addition, the peripheral threading according to the present invention ensures progressive opening of the slotted element, so that the positioning of the acetabular cup at the time of fitting is made more precise.

More particularly, the intermediate element is a hollow core with a hemispherical outer surface and is able to come into contact against at least one internal meridian generatrix of each segment defined by two consecutive expansion slots of the artificial acetabular cup. This intermediate core is preferably a solid component whose outer surface is continuous. All the internal surfaces of the acetabular cup are advantageously in contact with the outer surface of the core when the latter is screwed fully and positioned in the acetabular cup.

To permit this screwing, the inner part near the opening of the hollow acetabular cup comprises a threading in which said intermediate core is screwed, said intermediate core also having a corresponding threading in the area of its upper outer edge and surrounding its own opening, and the internal diameter of the opening of said acetabular cup in the standby position before screwing of said intermediate core is smaller than the external diameter of this intermediate core.

The result is a novel expansible acetabular prosthesis with double mobility which affords solutions to the problems which are posed by the disadvantages of the present prostheses set out above: this is because the three elements which make up the prosthesis according to the invention are all of congruent and engageable hemispherical shape. Thus, because of the continuous contact of the outer surface of the intermediate component with the inner surface of the lower acetabular cup, and which are perfectly congruent once in place, a better bearing is obtained than in the case when the intermediate component is only a ring and/or is fixed to the acetabular cup only by way of threads permitting their respective screwing. The present invention avoids any mobility and displacement between these components over the course of time.

Moreover, the continuous inner surface of the intermediate element similarly permits a perfect congruence of the plastic insert, which will therefore not be at risk of creeping or catching on any roughening of the intermediate element.

The fact that the three components of the prosthesis according to the present invention are in contact and congruent with one another ensures contact without elasticity: this concept is very different from most of the patents published on this type of prosthesis and even runs counter to the teaching published to date, for example that of patent EP 640325, since these documents, by contrast, generally strive for a minimum of elasticity between the different components.

By virtue of this engagement and the congruence of the intermediate element with the acetabular cup, the present invention makes it possible to regulate the orientation of the insert which then receives the head ball of the joint, as is described in the preceding patent application by M. Chauvin, cited above.

Moreover, the particular position and arrangement of the outer anchoring and pre-impaction teeth of the acetabular cup according to the present invention make it possible, on the one hand, to place the latter in the bone cavity easily and precisely by simple bearing on the bottom of the latter without having to form a thread in the wall of this cavity, thereby permitting stabilization of the acetabular cup in the bone so that screwing of the intermediate elements is possible, and, on the other hand, to anchor in this bone cavity by expansion during screwing of the intermediate core, the orientation of the fins which form said anchoring teeth ensuring both anti-rotation and anti-extraction of said acetabular cup. Very effective initial stability is obtained by virtue of the join thus obtained between the prosthesis and the bone.

In a particularly advantageous embodiment, the anchoring teeth are distributed uniformly over the outer surface of said segments of the artificial acetabular cup toward its opening, and, before screwing, the distal ends of said anchoring teeth are situated inside the enveloping surface, preferably an enveloping sphere of diameter $D_5$ corresponding to the position of the outer surface of the acetabular cup once expanded by screwing of the intermediate element.

More particularly, the anchoring teeth arranged on the outer surface of the segments toward the opening of the acetabular cup are formed as fins, some being symmetrical with respect to a meridian plane passing through the polar axis of the acetabular cup, and the others being symmetrical with respect to a plane perpendicular to said axis.

According to an advantageous alternative embodiment of the invention, said segments preferably comprise impaction teeth consisting of spikes situated in the polar zone of the outer surface of the acetabular cup.

The zone near the opening of the acetabular cup, in which the anchoring teeth are arranged, and the polar zone, in which the impaction teeth are arranged, are delimited by a plane perpendicular to the polar axis in a proportion of 2/3 to 2/5 for the zone near the opening and of 1/5 to 1/3 for the polar zone.

Said impaction spikes are arranged in a vertical direction or an intermediate direction between the vertical direction of the polar axis and the radial direction of said sphere of diameter and the bone-anchoring teeth are arranged in a radial direction or an intermediate direction between said radial direction and the direction perpendicular to the polar axis.

In an advantageous embodiment, the inner surface of said intermediate element is solid and polished, and said insert consists of a cup, which is fixed or movable, preferably movable, whose outer surface is the shape of a smooth spherical cap and which has a cavity with a smooth spherical inner surface.

The possibility of using a movable cup articulating with the inner surface of the polished intermediate element permits greater stability of the prosthetic articulation upon extreme movements, which reduces the risk of luxation.

In another embodiment, it is possible to use a fixed insert: in this configuration the invention also affords the advantage of perfect congruence between the insert and the cup, so as to reduce wear and creep.

The characteristics according to which the inner surface of the intermediate element is smooth and/or this surface is solid, that is to say perfectly regular and nonperforated, with no roughness or cavity (screw hole), represent an important advantage because this avoids the production of debris from wear of the insert, particularly when it is made of polyethylene.

BRIEF DESCRIPTION OF THE DRAWINGS

Other characteristics and advantages of the present invention will become evident on reading the following detailed description in which reference is made to FIGS. 1 to 3.

FIG. 1 is a cross section showing the acetabular prosthesis according to the invention, introduced into the cavity of the iliac bone of a patient who has already been operated on.

DESCRIPTION OF THE PREFERRED EMBODIMENTS

Figure 1:
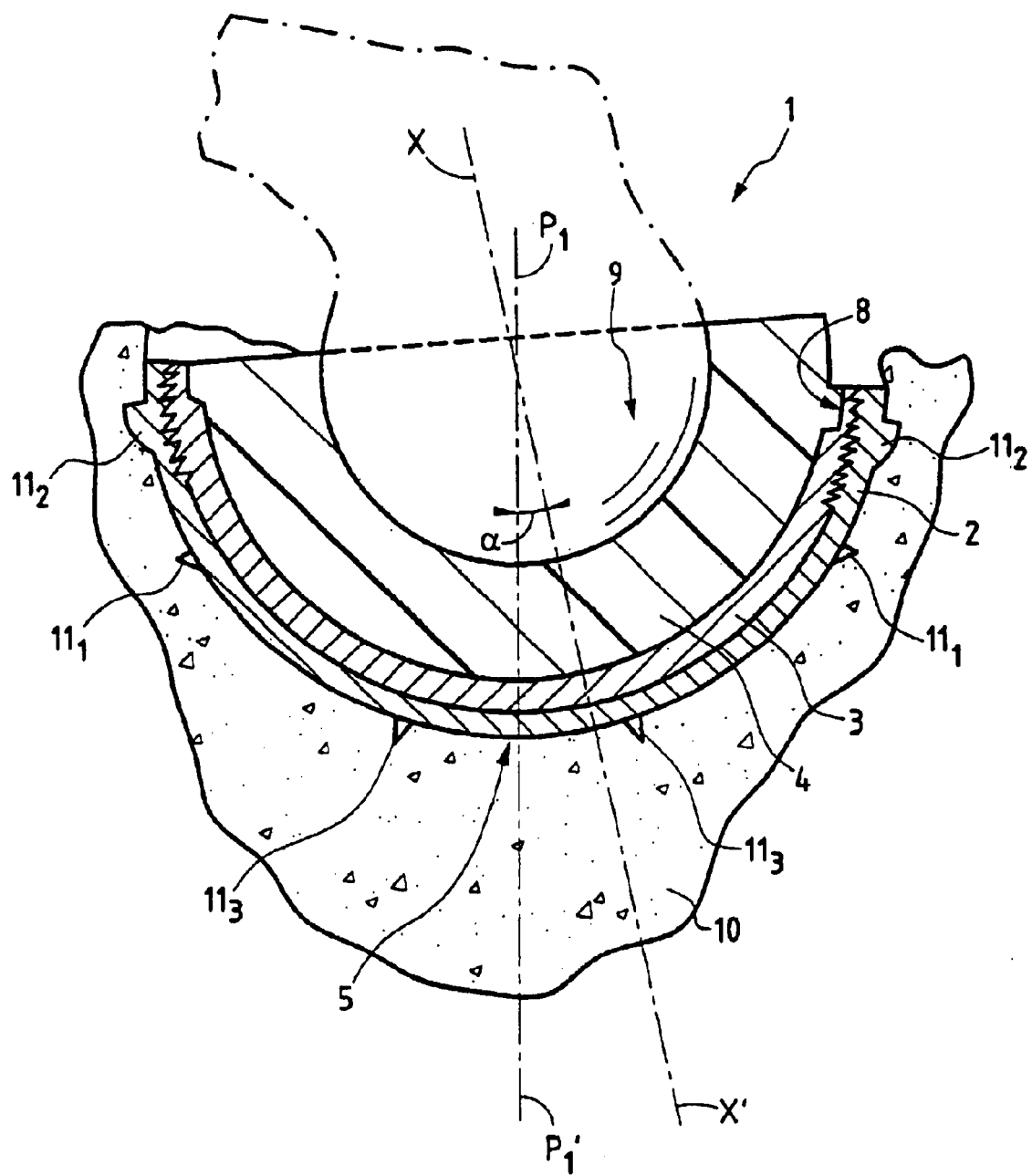

The expansible acetabular prosthesis 1 is of the type comprising a hollow artificial acetabular cup 2 in which an intermediate element 3 is screwed which receives an insert 4, likewise hollow and made of plastic, such as polyethylene, or of other materials such as ceramic.

The artificial acetabular cup 2 and the intermediate element 3 are preferably made of a biocompatible metal.

The artificial acetabular cup 2 in the shape of a hollow cap has a certain number of expansion slots 6 which are uniformly and symmetrically distributed over its periphery: the slots 6 are formed in the direction of the pole $P_2$ of the acetabular cup in such a way as to form a segment 7 between each slot, all of these segments being integral with the polar cap $P_2$ which is thus nondeformable in this zone and whose external diameter $D_5$ corresponds to the diameter of the bone cavity 5 made in the iliac bone 10 in order to receive said prosthesis. This polar zone $P_2$ is of course situated on the polar axis $P_1$, $P_1'$ of the prosthesis and remote from the different openings of the different components of which the prosthesis is made up.

Figure 2A:
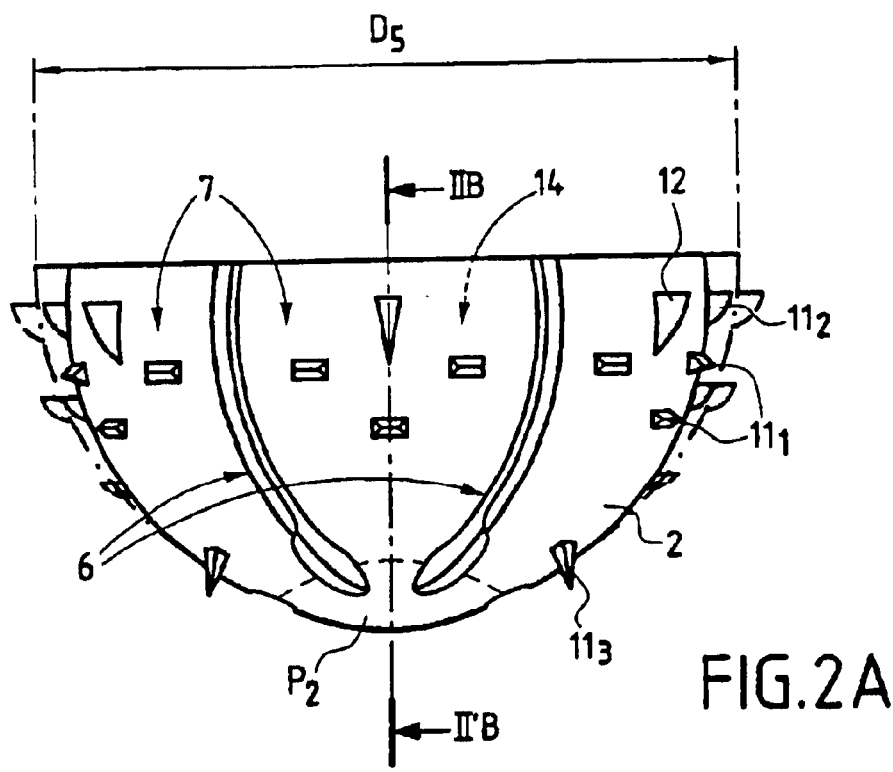
FIGS. 2a and 2b show a side view and a cross section, respectively, of an artificial acetabular cup according to the invention.
Figure 2B:
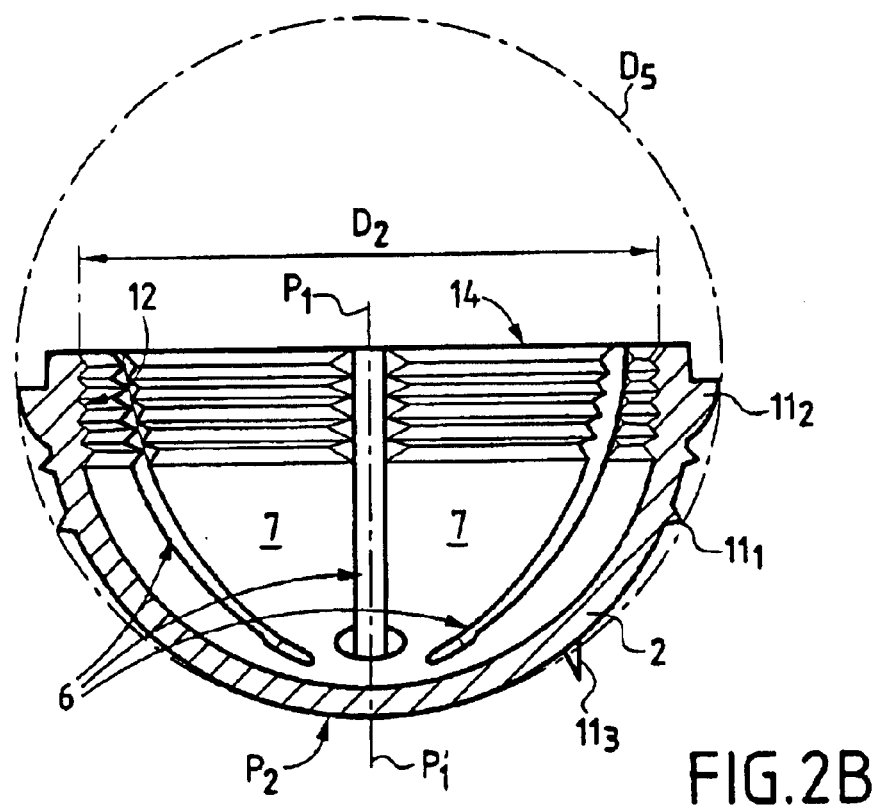

As are represented in FIG. 2b, the distal ends of the anchoring teeth $11_1$ and $11_2$ arranged toward the opening 14 of the artificial acetabular cup 2 are situated inside the enveloping sphere of diameter $D_5$ corresponding to the position of the outer surface of the acetabular cup 2 once it has been expanded by the intermediate element 3: this facilitates insertion of the acetabular cup into the bone cavity 5. By contrast, the spike-shaped impaction teeth $11_3$ situated on the segments 7 toward the polar zone $P_2$ of said acetabular cup 2 protrude from said enveloping sphere of diameter $D_5$ in order to be impacted directly into the bone cavity 5 upon fitting of said acetabular cup 2 at the bottom of the latter and to ensure an initial immobilization.

The zone near the opening 14 of the acetabular cup 2 in which the anchoring teeth $11_1$ and $11_2$ are arranged and the polar zone $P_2$ in which the impaction teeth 11 are arranged are delimited by a plane perpendicular to the polar axis $P_1$, $P_1'$ in a proportion of 3/4 for the zone near the opening 14 and of 1/4 for the polar zone, that is to say the polar zone occupies a height, along the polar axis from said pole, corresponding to 1/4 of the total height.

In FIGS. 2A and 2B, said polar zone $P_2$ of the acetabular cup 2 on which the impaction teeth $11_3$ of the acetabular cup 2 in the bone cavity are arranged is a spherical cap and forms, with the distal ends of the bone-anchoring teeth $11_1$ and $11_2$ arranged outside said polar zone $P_2$ toward the opening of the acetabular cup 14, in the standby position before screwing, a sphere of diameter D5 corresponding to the position of the outer surface of said acetabular cup 2 after screwing and anchoring of the teeth in the bone cavity, as is shown by broken lines in FIG. 2B.

Figure 3A:
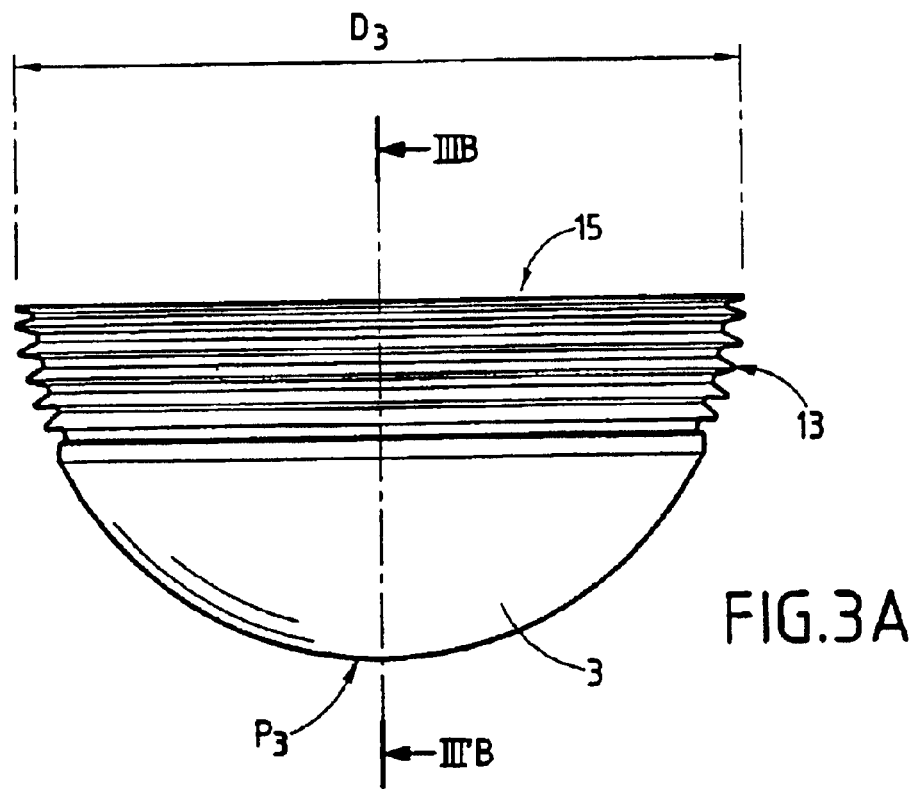
FIGS. 3a and 3b show a side view and a cross section, respectively, of an intermediate element according to the invention.
Figure 3B:
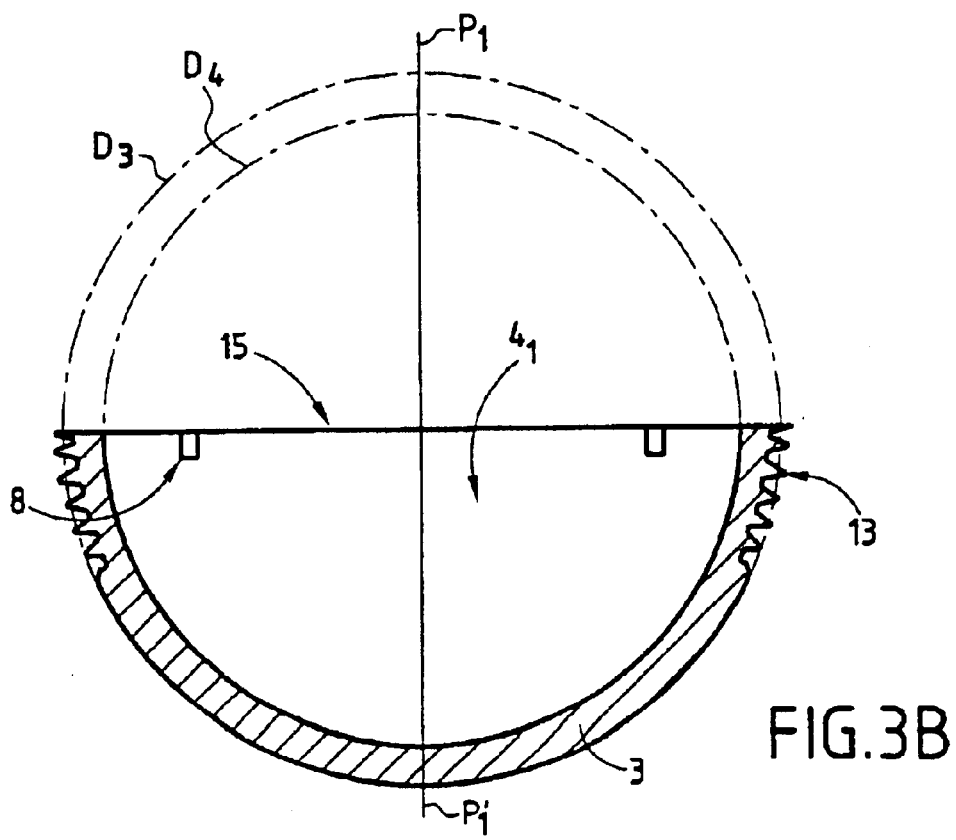

In FIG. 3, the intermediate element 3 has an external profile corresponding to the internal profile of the acetabular cup 2 once expanded, but with an external diameter $D_3$ which is greater than the internal diameter $d_2$ of said acetabular cup at the area of the opening 14 thereof when it is in the standby position, for example when placed inside the cavity 5 and against the bottom thereof: thus, when the intermediate element 3 is screwed inside the acetabular cup 2, said segments 7 are gradually spread apart as the threads of the threading 13 of the intermediate element 3 engage in those of the threading 12 of the acetabular cup 2 as a result of their divergent profile on the outer spherical surface of said intermediate element. The gradual spreading apart of said segments 7 which is thereby obtained by screwing the intermediate element 3 into the acetabular cup 2 permits flexible and stress-free fixation by gradual anchoring of the teeth $11_1$ and $11_2$ in the wall of the bone cavity 5 until the inner surface of the acetabular cup corresponds to the outer surface of the intermediate element 3, the two surfaces then having the same diameter $D_3$ and the external diameter of the acetabular cup having simultaneously reached that $D_5$ of the bone cavity 5.

Those anchoring teeth 11 arranged on the outer face of the segments 7 toward the opening 14 of the acetabular cup 1 are formed as fins, some of which $11_2$ are arranged in meridian planes passing through the polar axis $P_1$, $P_1'$ of the acetabular cup 2 and ensure an anti-rotation function, while the others $11_1$ are in parallel planes perpendicularly intersecting the axis $P_1$, $P_1'$ and ensuring the anti-extraction function.

Once the intermediate element 3 has been screwed fully into the artificial acetabular cup 2, their respectively outer surface $D_3$ and inner surface $d_2$ being in continuous contact, it is possible to introduce the plastic insert 4 into the intermediate element 3 via its opening 15, and the inner surface of the element 3 and the outer surface of the insert 4 are of the same diameter $D_4$ and also come into contact with one another.

This insert 4, preferably made of plastic, itself comprises at its center a cavity 9 which is able to receive the prosthetic head represented in broken lines in FIG. 1. To produce a fixed insert, the insert 4 will comprise appendices arranged in a crown formation on its outer face and uniformly distributed over its periphery: these appendices have an outer profile identical, except for play, to that of notches 8 formed in the intermediate element 3, around and at the edge of its opening 15, and in which said appendices of the insert 4 are accommodated: the inclination of the crown comprising said appendices in relation to the polar axis XX' of the insert 4 makes it possible to adjust the angle thereof in relation to the polar axis P1, P'1 of the intermediate element 3 and of the acetabular cup 2; likewise, as regards the angular position of the appendices in relation to the notches 8, to adjust the angle of rotation of the insert 4 about the polar axis $P_1$, $P'_1$; this being described in patent application FR 2 700 946 by M. Chauvin. Means for fixing and locking said insert 4 in relation to the intermediate element 3 are also described in this patent application FR 2 700 946.

In an alternative embodiment, the inner surface of the acetabular cup 2 and the outer surface of the intermediate element 3 have a partially frustoconical shape or the shape of a nonspherical cap of ovoid curvature, but preferably with a circular opening of internal diameter $d_2$.

The insert 4 can be made of ceramic material.

The outer surface of said artificial acetabular cup 2 can be treated with a biomaterial which promotes osseointegration, for example hydroxyapatite (HAP).

Finally, lugs and/or hooks can be added and arranged in the zone near the opening 14 of the acetabular cup 2.

What is claimed is:

1. An expansible acetabular prosthesis comprising:
   a hollow metal artificial acetabular cup having expansion slots distributed over its periphery;
   a metal intermediate cup-shaped element with an inner surface of spherical cap shape,
   a hollow polyethelene insert with outer and inner surfaces of spherical cap shape fitting in said metal intermediate element;
   wherein said metal acetabular cup and said metal intermediate element comprise screwing means for bringing an outer surface of said metal intermediate element into congruent contact, by screwing, against at least one internal meridian generatrix of each segment delimited by two consecutive said slots,
   wherein said screwing means comprise a peripheral threading formed on the inner surface of said metal acetabular cup near its opening, in which threading said metal intermediate element is screwed with the aid of a complementary threading on its outer surface near its opening,
   wherein an internal diameter ($d_2$) of the opening of said metal acetabular cup in a standby position before screwing said intermediate element therein is smaller than an external diameter ($D_3$) of said metal intermediate element, and
   wherein said metal acetabular cup is equipped with bone-anchoring teeth on its outer face.

2. The acetabular prosthesis as claimed in claim 1, wherein said intermediate element is a solid component whose outer surface is continuous.

3. The acetabular prosthesis as claimed in claim 2, wherein all the inner surfaces of the acetabular cup are in contact with the outer surface of the intermediate element when the intermediate element is fully screwed and positioned in the acetabular cup.

4. The acetabular cup as claimed in claim 1, wherein the inner surface of the acetabular cup and the outer surface of the intermediate element are of spherical cap shape.

5. The acetabular prosthesis as claimed in claim 1, wherein the anchoring teeth are distributed uniformly over the outer surface of said segments of the artificial acetabular cup toward its opening, and, before screwing, the distal ends of said anchoring teeth are situated inside an enveloping sphere of diameter ($D_5$) corresponding to the position of the outer surface of the acetabular cup once expanded by screwing of the intermediate element.

6. The acetabular prosthesis as claimed in claim 1, wherein the anchoring teeth arranged on the outer surface of the segments toward the opening of the acetabular cup are fins, some of said fins being symmetrical with respect to a meridian plane passing through a polar axis of the acetabular cup and others of said fins being symmetrical with respect to a plane perpendicular to said polar axis.

7. The acetabular prosthesis as claimed in claim 1, wherein said segments comprise impaction spikes situated in a polar zone of the outer surface of the acetabular cup.

8. The acetabular prosthesis as claimed in claim 7, wherein a zone near the opening of the acetabular cup in which the anchoring teeth are arranged, and the polar zone are delimited by a plane perpendicular to a polar axis of the acetabular cup in a proportion of 2/3 to 2/5 for the zone near the opening and of 1/5 to 1/3 for the polar zone.

9. The acetabular prosthesis as claimed in claim 7, wherein said polar zone is a spherical cap and forms, with the distal ends of the bone-anchoring teeth in the standby position before screwing, a sphere of diameter ($D_5$) corresponding to the position of the outer surface of said acetabular cup after screwing and anchoring of the teeth in the bone cavity.

10. The acetabular prosthesis as claimed in claim 7, wherein said impaction spikes are arranged in a vertical direction of a polar axis of the acetabular cup or an intermediate direction between the vertical direction and the radial direction of a sphere of diameter ($D_5$) and
    the bone-anchoring teeth are arranged in the radial direction or an intermediate direction between said radial direction and the direction perpendicular to the polar axis.

11. The acetabular prosthesis as claimed in claim 1, wherein the inner surface of said intermediate element is solid and polished, and said insert comprises a cup whose outer surface is the shape of a smooth spherical cap and which has a cavity with a smooth spherical inner surface.

12. The acetabular prosthesis as claimed in claim 1, wherein said artificial acetabular cup and said intermediate element are made of biocompatible metal.

13. The prosthesis as claimed in claim 1, wherein the artificial acetabular cup is covered with a biomaterial which promotes osseointegration.

14. An expansible acetabular prosthesis comprising:
    a hollow metal artificial acetabular cup having expansion slots distributed over its periphery and a metal cup-shaped intermediate element in said acetabular cup, said metal acetabular cup having bone-anchoring teeth on an outer surface;
    an inner surface of said metal acetabular cup and an outer surface of said metal intermediate element having corresponding threads by which said metal intermediate element is screwed into attachment with said metal acetabular cup, wherein before said metal intermediate element is screwed into said metal acetabular cup an internal diameter of an opening of said metal acetabular cup into which said metal intermediate element is screwed is smaller than an external diameter of said metal intermediate element;
    first connectors on an inner surface of said metal intermediate element; and
    a polyethylene cup-shaped insert in said metal intermediate element, an outer surface of said polyethylene insert having second connectors that correspond to and join said first connectors and that are positioned to define an orientation of said polyethylene insert relative to said metal intermediate element.

15. The acetabular prosthesis of claim 14, wherein said first connectors are notches and said second connectors are projections.

* * * * *